(12) United States Patent
Rushing

(10) Patent No.: US 6,671,052 B1
(45) Date of Patent: Dec. 30, 2003

(54) MULTI-CHANNEL DENSITOMETER

(76) Inventor: Allen Joseph Rushing, 429 Tara La., Webster, NY (US) 14580

(*) Notice: Subject to any disclaimer, the term of this patent is extended or adjusted under 35 U.S.C. 154(b) by 304 days.

(21) Appl. No.: 09/873,465

(22) Filed: Jun. 4, 2001

(51) Int. Cl.$^7$ ................ G01N 21/47; G01N 21/84
(52) U.S. Cl. ................ 356/446; 356/429; 356/430
(58) Field of Search .................. 356/443, 444, 356/223, 429, 430, 431, 445, 446, 447, 448; 346/33 A, 49; 250/226, 214 D, 214 C, 214 R; 399/74, 78, 64, 49

(56) References Cited

U.S. PATENT DOCUMENTS

| | | | |
|---|---|---|---|
| 3,995,958 A | | 12/1976 | Pfahl et al. |
| 4,003,660 A | | 1/1977 | Christie, Jr. et al. |
| 5,075,725 A | | 12/1991 | Rushing et al. |
| 5,237,181 A | * | 8/1993 | Kerkhoff et al. ....... 250/559.08 |
| 5,402,361 A | | 3/1995 | Peterson et al. |
| 5,471,282 A | * | 11/1995 | Hayashi et al. ............ 399/64 |
| 5,546,165 A | | 8/1996 | Rushing et al. |
| 5,854,680 A | * | 12/1998 | Rakitsch .............. 356/406 |
| 5,903,796 A | * | 5/1999 | Budnik et al. ............ 399/26 |
| 5,933,682 A | | 8/1999 | Rushing |
| 5,983,044 A | | 11/1999 | Kodama et al. |
| 5,988,067 A | | 11/1999 | Ishida et al. |
| 6,144,024 A | * | 11/2000 | Rushing ............ 250/214 DC |
| 6,229,972 B1 | * | 5/2001 | Rushing .............. 399/74 |
| 6,370,408 B1 | * | 4/2002 | Merchant et al. ......... 600/322 |
| 6,427,057 B1 | * | 7/2002 | Hameister et al. ........ 399/74 |
| 6,505,010 B1 | * | 1/2003 | Izumizaki et al. ........ 399/39 |

OTHER PUBLICATIONS

U.S. patent application Ser. No. 09/543,094, Rushing, pp.2–7, 12–17; Figs. 3–8.

Dimitry Gorinevsky, Performance Analyst of Cross–Direction Process Control'Using Multivariable and Spectral. Models, IEEE Transactions on Control system Technology, Jul. 2000, pp. 589–600, vol. 8, No. 4, IEEE, Inc., 3 Park Ave., New York, NY 10016.

Allen Rushing, "Trade–Offs in On–Board Densitometry," IS&T's NIP16: International Conference on Digital; Printing Technologies, Oct. 15–20, 2000, pp. 652–656, IS&T The Society for Imaging Science and Technology, Springfield, VA.

* cited by examiner

Primary Examiner—Russell Adams
Assistant Examiner—Andrew Sever

(57) ABSTRACT

A multi-channel densitometer has a light sensor for each channel. The channels may be on a single circuit board, or may be on small, independently locatable probes. The outputs from the sensors are input to a single conveniently located controller circuit. The controller circuit provides power and control signals to the sensors, and processes the sensor outputs to obtain sample optical density. The multi-channel configuration saves space where the density measurements are needed, reduces the component count and cost, and facilitates calculation of multi-channel density functions, such as uniformity, transfer efficiency and color balance.

20 Claims, 8 Drawing Sheets

MULTI-CHANNEL DENSITOMETER

CROSS REFERENCE TO RELATED APPLICATIONS

Reference is made to co-pending U.S. Patent Application, filed on Mar. 11, 2002 in my name as follows:

Ser. No. 10/095,166, entitled DIGITAL DENSITOMETER USING LIGHT-TO-FREQUENCY CONVERTER.

FIELD OF THE INVENTION

This invention relates generally to densitometers for measuring optical density. In particular, the invention relates to optical density measurement of multiple spots or test patches for monitoring and quality control of printed output.

BACKGROUND OF THE INVENTION

In printing and copying apparatus, machine parameters are adjusted, either manually or automatically, to produce images having well regulated darkness or optical density. Printer process control strategies typically involve automatically measuring the transmissive or reflective optical density of printed areas (called "test patches") as they are printed. Alternatively, printed samples may be measured manually using a "bench-top" densitometer. In either case, the density measurements are the basis for quality evaluation and control. Adjustments may then be determined to regulate the printed test patches to the desired density levels. The adjustments are often applied automatically, though some printer adjustments may require manual adjustment by an operator. For test and diagnostic purposes, large nominally uniform areas or multiple test patches may be printed to check for deviations from the desired uniformity.

In a large-format printer, uniformity may be difficult to maintain over the large printed areas, particularly in the direction perpendicular (cross-track) to the process direction. Nonuniformity can also be a problem in non-printed web production processes, such as plastic sheet, textiles, and paper. In these cases optical density measurements may be needed transversing the cross-track direction. U.S. Pat. No. 5,546,165, to Rushing et al uses a document scanner as a test print densitometer. Such a scanner may use an essentially continuous linear array of light sensors to collect measurements from several thousand picture elements or pixels spanning the cross-track dimension. These measurements provide the cross-track density "profile". This approach requires uniform illumination across the wide printed area, imaging optics, and a shift register driven to provide an output voltage signal representing the pixel-by-pixel cross-track profile of transmittance or reflectance.

A simpler and less expensive approach is to obtain representative cross-track measurements at just a few spots. Three or four representative cross-track measurements are sufficient to guide basic adjustments and/or maintenance on the typical machine. The objective of such basic adjustments and/or maintenance is typically to balance the average density edge-to-edge, and avoid a "high" or "low" spot in the center.

Adjustments to the engagement or spacing of the various work stations, relative to the image-bearing medium, are often used. Independent adjustments are often available at the front and back ends of a work station. An independent center adjustment may also be available. In an electrophotographic process, such adjustments may be applied to corona charging devices, to illumination or exposure, and to toning stations. Image exposure adjustments, gradual from edge-to-center-to-edge, are disclosed in U.S. Pat. No. 5,933,682 to Rushing, for example. In paper manufacturing processes discussed by Gorinevsky et al, sets of identical independent actuators, distributed across the paper web, control cross-track uniformity of web attributes at several production stages.

The electrophotographic printer described in U.S. Pat. No. 5,983,044 to Kodama et al has a densitometers positioned before and after transfer of the toned image from the photoconductor drum to the receiver. One densitometer is positioned to read test patches on the drum before transfer. Two more densitometers provide post-transfer readings of the transferred toner patch and the residual toner remaining on the photoconductor drum, respectively. Transfer efficiency is determined from these readings. Deviations from the normal transfer efficiency are the basis for electrical adjustments applied to the multi-color developing units and to the transfer process.

In a typical multi-color printer, test patches of each process color are monitored for process control purposes. Ideally, each color has its own dedicated densitometer channel, with a light emitter color or peak emission wavelength selected for high sensitivity of the readings. Separate dedicated channels may also enable density readings to be taken farther upstream in the imaging process, in the individual color processing modules, before the separations are collected on a single web. The earlier upstream readings minimize the delay in obtaining measurements, and enable faster-responding feedback control loops for the process.

An economical single-channel densitometer for an electrophotographic color printer is disclosed in U.S. Pat. No. 5,075,725 to Rushing et al. The transmission densitometer has an infrared emitter and measures test patches covered with cyan, magenta, or yellow toner. Previously stored base density readings from untoned film are subtracted to yield net toner densities. The machine logic keeps track of the color of the passing patches, so that the measured net toner densities can be compared to target values for the respective colors.

This single-channel infrared-emitting densitometer outputs usable density signals for patches covered with the colored toners, and black toner. However, colorants in other applications, such as ink jet inks, do not sufficiently block infrared light. Even for unfused colored toners, better sensitivity is obtained using emitters of complementary color to the respective test patches, i.e., red, green, and blue emitters for cyan, magenta, and yellow toner, respectively. Finally, the single-channel configuration does not address the need in some printer configurations for density readings at multiple positions.

The approach described in U.S. Pat. No. 3,995,958 to Pfahl et al obtains good color sensitivity. Filters of complementary colors to the test patches automatically rotate into position in front of a white light emitter, so that each colored patch is read with light of the particular color for highest sensitivity. While using only one densitometer, this approach requires bulky, complicated, and expensive mechanisms to change filter positions at the appropriate times. Furthermore, all the variously colored patches must be on the same single track of the moving medium, and pass the densitometer one after another. Such a fixed-position single-channel configuration cannot address needs for density readings in multiple in-track or cross-track positions.

As an alternative to the white light source and multiple color filters used in U.S. Pat. No. 3,995,958 by Pfahl et al, multiple emitters of different colors can be used, e.g., red, green, and blue LEDs. These emitters are aimed such that transmitted or reflected light is collected by a single photodetector. To read cyan, magenta, and yellow test patches, a single complementary-colored LED is energized, according to the known color of the test patch to be read at that time. A test patch of mixed or layered colorants is read by rapidly and successively energizing the LEDs one at a time, to obtain a set of density readings characteristic of the overall test patch color while the test patch is in position. Such a configuration measures test patches of various colors without the complexity of mechanical motion in the densitometer, but otherwise is subject to the same limitations as other fixed-position single-channel configurations.

Using mechanical drives, a single-channel densitometer configuration can be adapted to obtain readings at different positions. In U.S. Pat. No. 4,003,660, Christie et al disclose a densitometer movably mounted on support members that extend across the width of a printed web. Such a mechanical drive is bulky, complicated, and expensive. Optical spacing and alignment tolerances are-more difficult to maintain, owing to the motion. At any given time, readings can be obtained at only one position, and time is required to move to the next position.

Multiple densitometers have been incorporated into computer networks, as in U.S. Pat. No. 5,402,361 to Peterson et al. Such networks facilitate consolidation of data into a central collection point, or host computer, for data logging, printing, evaluation, and process control purposes. The host computer in such a network processes signals for the individual connected densitometers, and can also compute multi-channel functions requiring data from two or more densitometers. A simple example of a multi-channel function is the density difference between two densitometers. However, such networks alone do not reduce the cost of the densitometers themselves.

Many document reproduction centers, printing shops, and graphic arts work areas have multiple printers, with many of the printers requiring at least one "on-board" densitometer. In both on-board and bench-top applications, multi-channel densitometry facilitates uniformity evaluation and multicolor test patch measurements. However, the cost of multiple densitometers, or multi-channel densitometry, is considerable and often prohibitive.

High cost (typically $1000 or more each) has not been a serious deterrent to the use of bench-top densitometers in professional laboratories. However, in more cost-sensitive environments, such as amateur photography labs, graphic arts studios, and student laboratories at educational institutions, bench-top densitometer cost has been an obstacle. On-board densitometers, specialized for use in a specific machine, and with minimal or no operator interfaces, can be much less costly than general-purpose bench-top instruments. Nevertheless, cost is an obstacle to their wide use within moderately priced copiers, printers, and other products. Cost issues are multiplied, of course, when multichannel densitometry is needed.

Advancing component technologies are reducing the aforementioned cost barriers, making densitometers cost-effective in an increasing range of applications. On-board densitometers have gradually penetrated the printer market, down even to some moderately priced printers. Less costly and more reliable LEDs are now often used instead of incandescent lamps as densitometer light emitters. Photo-diode light detectors are smaller and less costly than the photomultiplier tubes used in some older dk densitometers.

Application of digital electronics to densitometers eliminates the need for the costly analog logarithmic amplifier used in traditional analog designs. For example, U.S. patent application Ser. No. 10/095,166 of Rushing discloses an all-digital approach based on a light-to-frequency (L-to-F) converter electrically interfaced to a microcontroller and utilizing a look-up table (LUT). Despite these cost-reducing advances, densitometer cost is still an issue in printer design, particularly when multiple densitometers are considered for moderately priced products. The cost of bench-top densitometry, particularly multi-channel densitometry, also remains an issue in amateur photo labs, student laboratories, and other cost-sensitive areas.

SUMMARY OF THE INVENTION

One object of the present invention is to reduce densitometer cost for density measurement at multiple positions, for both bench-top and on-board applications. A single controller circuit, preferably with a digital microcontroller, provides electrical power, control signals, and sensor signal processing for multiple channels with preferably digital light detectors in one or more probes. With the preferable digital light detectors, the costly analog logarithmic amplifiers of traditional analog densitometers are eliminated. The controller circuit may be located on a probe along with the sensors for one or more channels, or may be on a separate connected circuit board. In either case, the components of the controller circuit are not replicated for each channel, further cutting costs.

Typically, the densitometer measurement channels are located on a single machine, or at a single bench-top work area. However, probes in multiple machines may also be connected to a single controller circuit, especially if the machines are close to each other and operated together.

Each densitometer probe contains at least one light sensor, in which the light-detecting component is preferably a small L-to-F converter integrated circuit. The corresponding light emitters, preferably LEDs, may also be included on the probe. The LEDs, if not a part of the probe, are separately mounted in positions that, align with the sensors on the probe when the probe is in its operating position. Separate LED mounting is sometimes preferable in a transmission mode of operation, where the LED and light detector are on opposite sides of the sample.

For mounting the probes, slide rails facilitate easy installation and removal, and establish a well-defined position relative to the sample to be measured. Alternatively, a mounting block at the connector end of the probe facilitates attachment to a support structure for cantilever mounting. The connector at the end of the probe is disconnected for easy probe removal, such as for cleaning. Should a probe become damaged or inoperative, only that one probe need be replaced—not the other probes or the separate controller circuit board.

Another object of the invention is a reduced space requirement at the measurement locations. By limiting the probe components and function to the minimum required to output digital signals responsive to light impinging on the light detectors, the probes can be made small. In particular, the probe width, in the process direction, can be minimized. An L-to-F converter in integrated circuit form, along with a controller circuit serving multiple channels, minimizes the total component count With a separate controller circuit board, the probe electronic components for each channel may consist of only the L-to-F converter, a decoupling capacitor, and the LED emitter with a series resistor (unless the LED is separately mounted). In some applications the probe may include additional sensor components such as light shields, lenses, and color filters.

With less space required by the densitometer probes, more space is available for various work stations, or for enabling overall reduction in machine size. Alternatively, the small probe may permit a needed density measurement where it could not be done with a bulkier complete densitometer. The small probe size, along with the electrical connector and mounting provisions, facilitate probe removal and replacement. Relocation of a probe to another measurement position is also easier, if that should be necessary.

Yet another object of the invention is to compute multi-channel, as well as single-channel, density functions in the densitometer controller circuit, where the density signals from all the channels are collected. Evaluations of uniformity or transfer efficiency, for example, require multi-channel density measurements. Only the required calculated results, measurement summaries, statistics, or exceptions are sent to the host computer or display device. This unburdens the host computer from such computations, allowing it to better and more timely attend to higher-level machine control functions. If the connection to-the host is wireless, outputting only summary data may also be advantageous in terms of reduced time duration of the transmission and/or reduced bandwidth.

Still another object of the invention is superior noise immunity, obtained by utilizing an all-digital approach. The issue of electrical noise immunity is heightened in multi-channel and multi-probe configurations, owing to the multiplicity of interconnections in the generally noisy environments inside printers or other machines. Electrophotographic printers, for example, contain noisy devices such as motors and corona chargers, mating noise immunity essential for accurate multi-channel densitometry. In some prior art densitometers, analog signals are switched, which can introduce additional transient noise or steady error. In the present invention, the preferred L-to-F converter integrated circuit has a digital (logic "high" or logic "low") frequency output The digital output has inherently better noise immunity than the analog input and output signals associated with the photodiodes, linear amplifiers, logarithmic amplifiers, and analog-to-digital converters of traditional densitometer designs. There is no switching of sensitive analog signals.

To obtain these objects, the multi-channel densitometer in the preferred embodiments utilizes an all-digital design and a single controller circuit to control and process signals to and from multiple measurement channels. The microcontroller of the controller circuit controls and processes signals individually for the channels, and also computes multichannel functions requiring readings from two or more channels. The L-to-F converter integrated circuits, one for each channel, provide digital frequency outputs. Control signals are also exclusively digital. This gives the multi-channel densitometer the superior noise immunity inherent in digital signals. The L-to-F converter integrated circuits also contribute to the minimal component count, small probe size, and economical cost.

The invention and its various advantages will become more apparent to those skilled in the art from the ensuing detailed description of the preferred embodiments, reference being made to the accompanying drawings.

BRIEF DESCRIPTION OF THE DRAWINGS

The subsequent description of the preferred embodiments of the present invention refers to the attached drawings wherein.

DETAILED DESCRIPTION OF THE PREFERRED EMBODIMENTS

Figure 1:
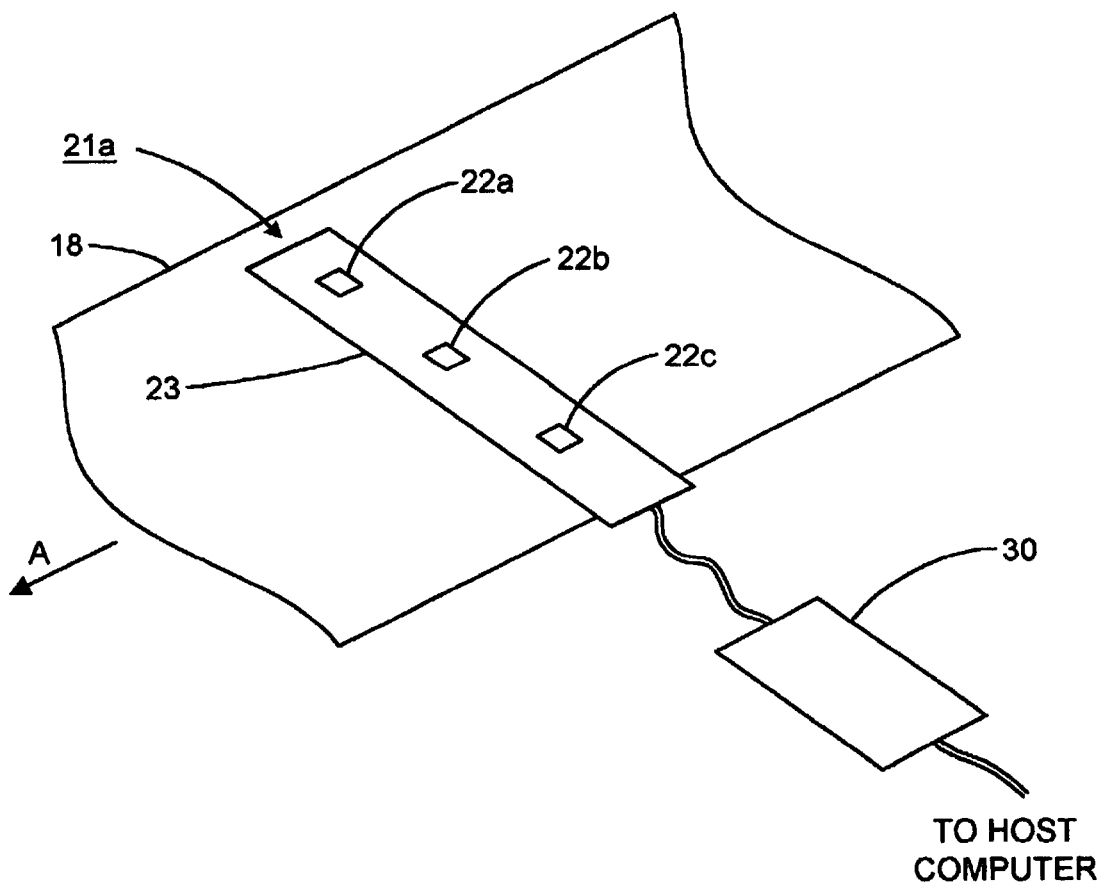
FIG. 1 is a multi-channel densitometer arrangement with a single sensor board, with sensors distributed across a moving web.

With reference to the portion of a wide-format machine shown in FIG. 1, a single probe 21a provides three channels of density measurements as web 18 advances in the direction shown by arrow "A". Each channel provides density measurement in either the reflection mode or the transmission mode. Probe 21a extends across web 18, with three sensors 22a, 22b, and 22c facing web 18 near the front edge, center, and rear edge. For reflection density measurement of the top side of web 18, light emitters, preferably LEDs, are mounted on circuit board 23, positioned and aligned to illuminate spots on web 18 opposite the respective sensors 22a, 22b, and 22c, as detailed in FIG. 7.

With continuing reference to FIG. 1, for transmission density measurement sensor circuit board 23 may be above web 18 as shown, or under web 18. Light emitters, preferably LEDs, on the opposite side of web 18 from sensor circuit board 23, are aligned so that light transmitted through web 18 impinges on respective sensors 22a, 22b, and 22c. The LEDs may be on a second probe circuit board (not shown in FIG. 1), as detailed in FIG. 6, or may be mounted separately from probe 21a, but aligned with it.

It should be appreciated that web 18 may represent part of a printing machine using any of the known printing or imaging technologies, such as electrophotography, ink jet, or lithography. Alternatively, web 18 may represent the product medium in a web production process or web transport process, without imaging, where web 18 advances through various production stages such as coating, drying, processing, and finishing. Paper, textile, plastic sheet, and photographic film production are examples of such web production processes. Web 18 may be measured "on-board", that is, within the machine, or may be removed to a bench-top or similar work surface for measurement. It should also be appreciated that while FIG. 1 shows a segment of a flexible web, multi-channel density measurements could be obtained similarly from samples in other forms, such as a rotating drum, for example.

Frequency outputs from sensors 22a, 22b, and 22c are all connected to controller circuit 30. Controller circuit 30 provides electrical power to all three channels, and receives a digital frequency output from each channel, with frequency proportional to the light impinging on the respective sensors. The light impinging on the L-to-F converter of each sensor is a portion of the light from an LED that has been transmitted through or reflected from web 18. Thus the frequency outputs are characteristic of the transmission or reflection optical density of the respective spots on web 18 transmitting or reflecting light to the sensors. Controller circuit 30 may also output digital control signals to the channels, such as programmable codes for sensitivity and frequency divide-by ratio, if the L-to-F converters are programmable in real time.

Controller circuit 30 may be on a separate circuit board from probe sensor circuit board 23, as shown. This configuration reduces the component count on circuit board 23, enabling a smaller circuit board area and the smallest probe. On the other hand, having a single circuit board is an advantage in some applications. If a somewhat larger probe 21a is acceptable, the components and functions of controller circuit 30 can be included on sensor circuit board 23.

Controller circuit 30 measures either the period or the frequency of the frequency outputs from the three channels of probe 21a Preferably the period is measured in terms of clock counts to yield a period count. The period count is utilized in entering a look-up table to obtain the scaled optical density value corresponding to web 18 transmittance or reflectance, using a circuit and a method such as disclosed in U.S. patent application Ser. No. 10/095,166. Controller circuit 30 also contains digital processing circuitry, preferably within a microcontroller, which computes, stores, compares, and otherwise processes the signals from all of the connected channels, according to the application.

In one typical application represented by FIG. 1, density readings are taken of normally processed areas that have the same nominal intended density, or special test patches that ideally have the same density. For each individual channel, the microcontroller computes statistics over a time interval, such as mean, maximum, minimum, range, and standard deviation. In addition, multi-channel statistics are computed, such as the average of all channel readings at a point in time, range of readings at a point in time, average over a time interval, and range of readings over a time interval. Other known statistical calculations may be programed according to the particular needs of the application.

Threshold values defining acceptable tolerances may be preprogrammed into the microcontroller. The microcontroller may then compare individual readings and statistics computed from many individual readings to the threshold values, and record the exceptions. Statistics and summaries are output from controller circuit 30 to receiving devices such as host computer, computer network, alphanumeric display, graphic display, and digital storage device. Connecting on to the receiving devices may be by cable as shown, or alternatively by wireless technology. The statistics and summaries are used in strategies for process monitoring and automatic control, manual machine adjustments and maintenance, and to support quality documentation and management.

In another typical application represented by FIG. 1, web 18 is a part of a color electrophotographic printer, with color separations collected on web 18. The three densitometer channels are dedicated to transmission density measurements of cyan, magenta, and yellow toned test patches, respectively. The LEDs associated with the respective channels are preferably of the complementary colors to the test patches, which in this case are red, green, and blue, respectively, to obtain high measurement sensitivity. If a black separation is printed, an infrared LED may be preferred for high sensitivity; in this context infrared may be considered, in a sense, a complementary color of black.

In such an application the density measurements may be used in a process control strategy as the basis for automatic adjustments to upstream color processing stations (not shown). The process control strategy may control each color separation independently, or may include functions of two or more colors, such as color balance functions. Examples of simple color balance functions are the three net toner density differences (cyan-magenta, cyan-yellow, and magenta-yellow). These differences are computed from color separation test patches which when overlaid by transfer to a receiver yield a nominally neutral or "balanced" gray patch. The empirically determined "balanced" values for these differences may be nonzero owing to non-ideal materials, processes, and instrumentation. Deviations of the measured differences from the target "balanced" values can be included among inputs to the calculation of adjustments to be applied to the color processing stations.

With all three channels in FIG. 1 connected to controller circuit 30, multi-channel functions such as color balance are readily computed in controller circuit 30. Only the final concise computed results, and not the extensive underlying raw data, need be output from controller circuit 30 to a host computer or display for determining process adjustments to be applied.

Figure 2:
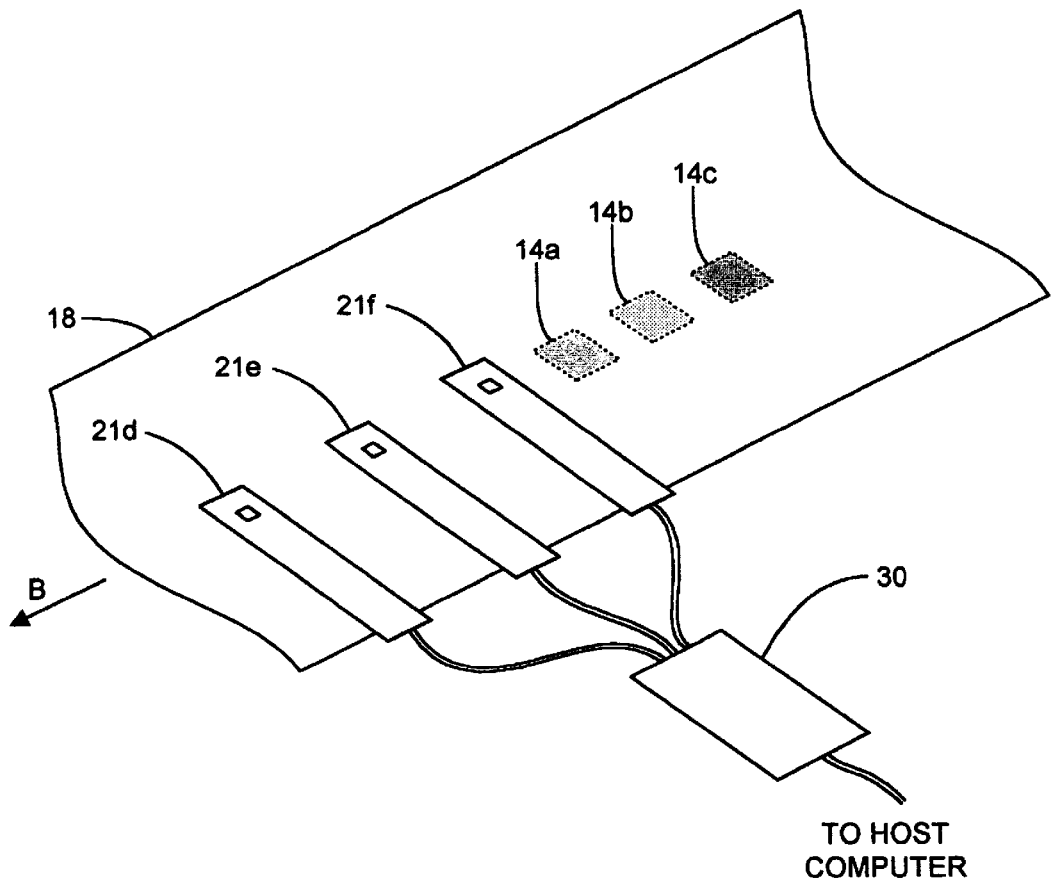
FIG. 2 is a multi-channel densitometer arrangement with probes positioned at different stages in the web process direction

Referring now to FIG. 2, densitometer probes 21d, 21e, and 21f are positioned at different stages in the process direction, where web 18 advances in the direction shown by arrow "B". The probes may be of either the type for transmission densitometry or for reflection densitometry. In a typical reflection density application, single-channel reflection density probes 21d, 21e, and 21f utilize red, green, and blue LEDs, respectively. All three probes are mounted to read in the same track. Sample areas of any color, either the normally processed web, or test patches such as patches 14a, 14b, and 14c on a reflective web support such as paper, pass opposite the sensors on probes 21d, 21e, and 21f successively.

Test patches 14a, 14b, and 14c may be formed of mixed or layered colorants. A set of three density readings from probes 21d, 21e, and 21f characterizes the composite color of each patch. With connections to all three probes, controller circuit 30 collects the set of three readings characterizing the test patch color. This three-channel densitometer thus functions as a basic colorimeter. Depending on the spectral emission of the LEDs and the spectral response of the detectors, such a calorimeter can approximate the color response of the human visual system to a range of variously colored samples.

In the case of separation test patches of a single colored toner, typically cyan, magenta, and yellow, only the measurements obtained using the complementary colored LED are normally needed. In this case separation test patches 14a, 14b, and 14c may be in different tracks, rather than the same track as shown in FIG. 2. If probes 21d, 21e, and 21f are fastened to a support structure just outside the edge of web 18, each probe has a length reaching to the track of its assigned color patches, positioning the sensor opposite the patches as they pass.

In the case where variability in the hue or saturation of the cyan, magenta, and yellow A-s separation colorants must be monitored, all three channels are used to read the separation patches. Other color separations, such as accent colors, "hi-fi" colors, or custom color separations of mixed colorants may also be monitored. All three probes are of length and position to read in the same track, as in the aforementioned colorimeter application, and as shown in FIG. 2.

Figure 3:
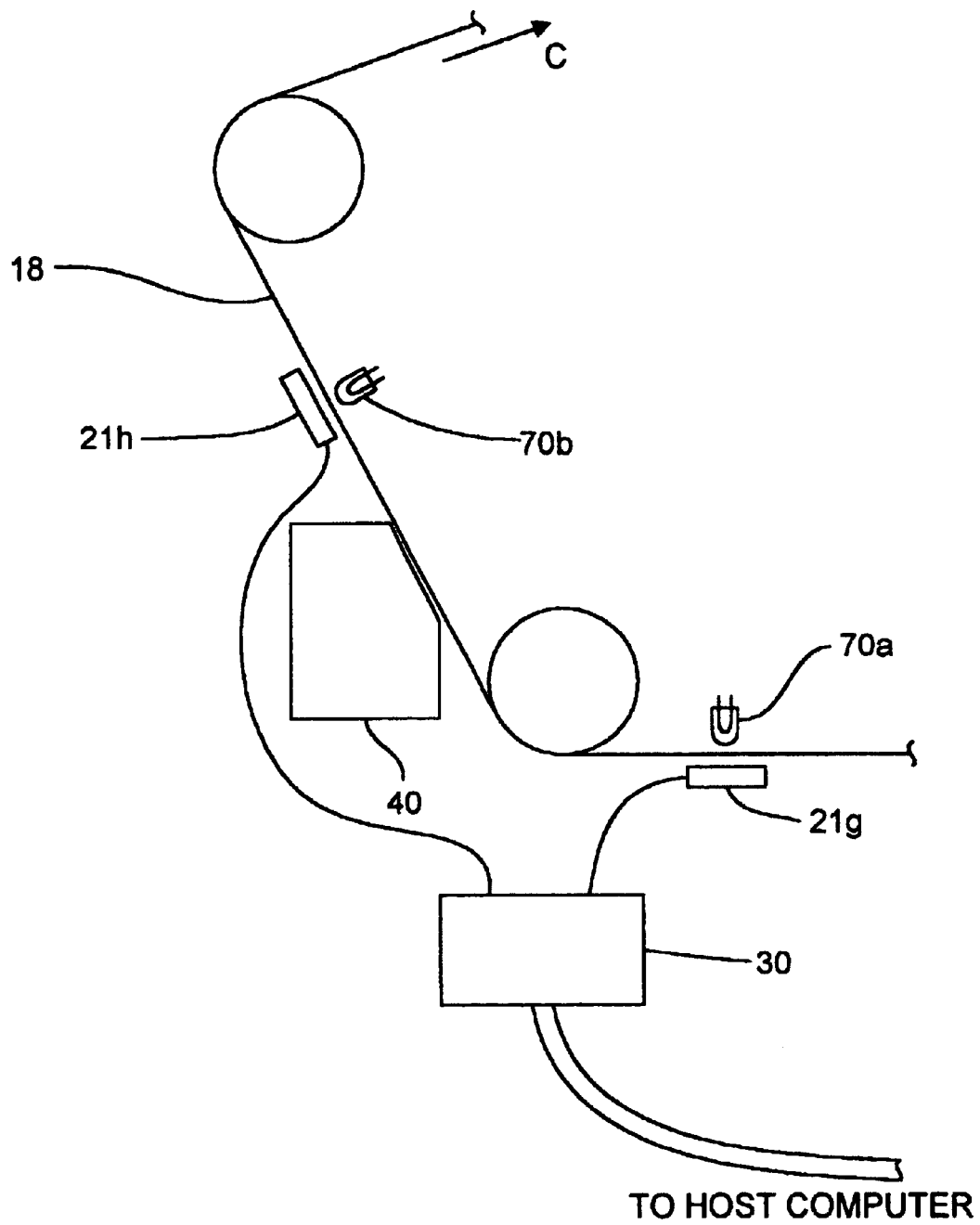
FIG. 3 is a multi-channel densitometer arrangement with probes positioned upstream and downstream from a work station.

Referring now to FIG. 3, densitometer probes 21g and 21h have sensors positioned in the 25 same track, upstream and downstream respectively from work station 40, with web 18 advancing in the direction shown by arrow "C". In a typical application, probes 21g and 21h have LEDs of the same color, and together monitor the change in density of web 18 attributable to work station 40. For any given spot on web 18 that passes probes 21g and 21h, the difference between readings, that is, the reading of probe 21h minus the reading of probe 21g, is attributed to work station 40.

Probes 21g and 21h may be of the transmission type, with LEDs 70a and 70b on the opposite side of web 30 from their respective sensor circuits, as shown. Alternatively, probes 21g and 21h could be of the reflection type. Controller circuit 30 collects readings from both probes, and performs the subtraction. Positive and negative differences are interpreted as the density increase or decrease, respectively, attributable to work station 40. These results are output to the host computer or display.

Figure 4:
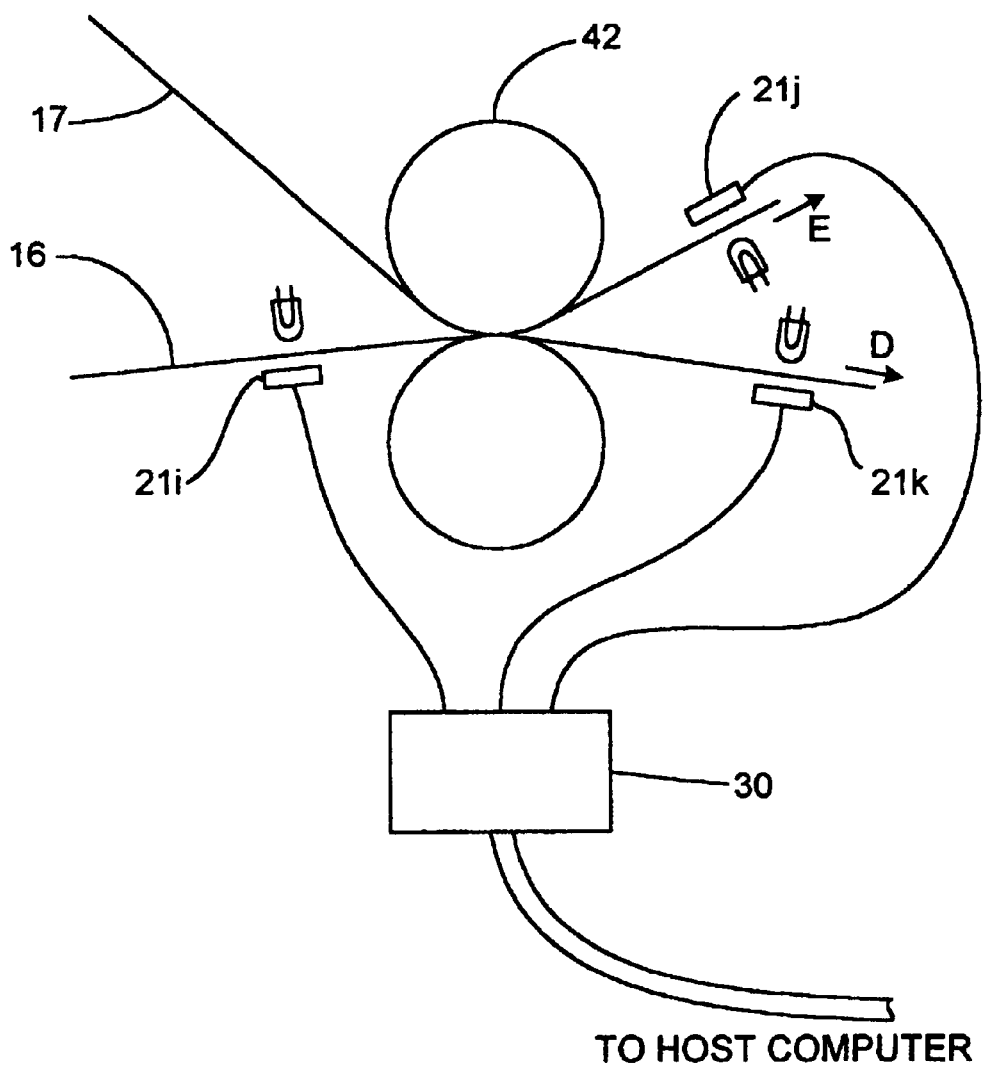
FIG. 4 is a multi-channel densitometer arrangement with probes positioned for pre-transfer and post-transfer measurements.

Turning now to FIG. 4, densitometer probes 21i, 21j, and 21k are positioned at different stages in the process direction, but with sensors in the same track, and have LEDs of the same color. Image web 16 and receiver web 17 advance in the directions shown by arrows "D" and "E", respectively. Such a configuration is typical of electrostatic roller transfer in an electrophotographic printer, where electrically biased transfer roller 42 LR transfers toner from image web 16 to receiver web 17. Probe 21i monitors pre-transfer transmission density on image web 16. Probe 21j monitors post-transfer transmission density on receiver web 17. Net toner density readings for probes 21i and 21j are obtained by subtracting the base density of the respective untoned supports from the density measurements of the toner-covered areas. The base density is typically measured some short time previous to the density measurement of the toner-covered area.

Transfer efficiency may be expressed as the ratio of net toner density readings of a given image area. In the configuration of FIG. 4, the post-transfer reading from probe 21j is divided by the pre-transfer reading of probe 21i. If the toner is completely transferred, the ratio is ideally 1.00, or 100% efficient. The difference between the pre-transfer reading of probe 21i and the post-transfer reading or probe 21j may also be used to evaluate transfer performance. Probe 21k is positioned to measure the residual toner density remaining on image web 16 after transfer. Readings from probe 21k can be used along with readings from probes 21i and 21j to evaluate transfer performance. All of these readings are collected in controller circuit 30, where multi-channel functions such as transfer efficiency are readily computed, and summary results subsequently output to the host computer or display.

Figure 5:
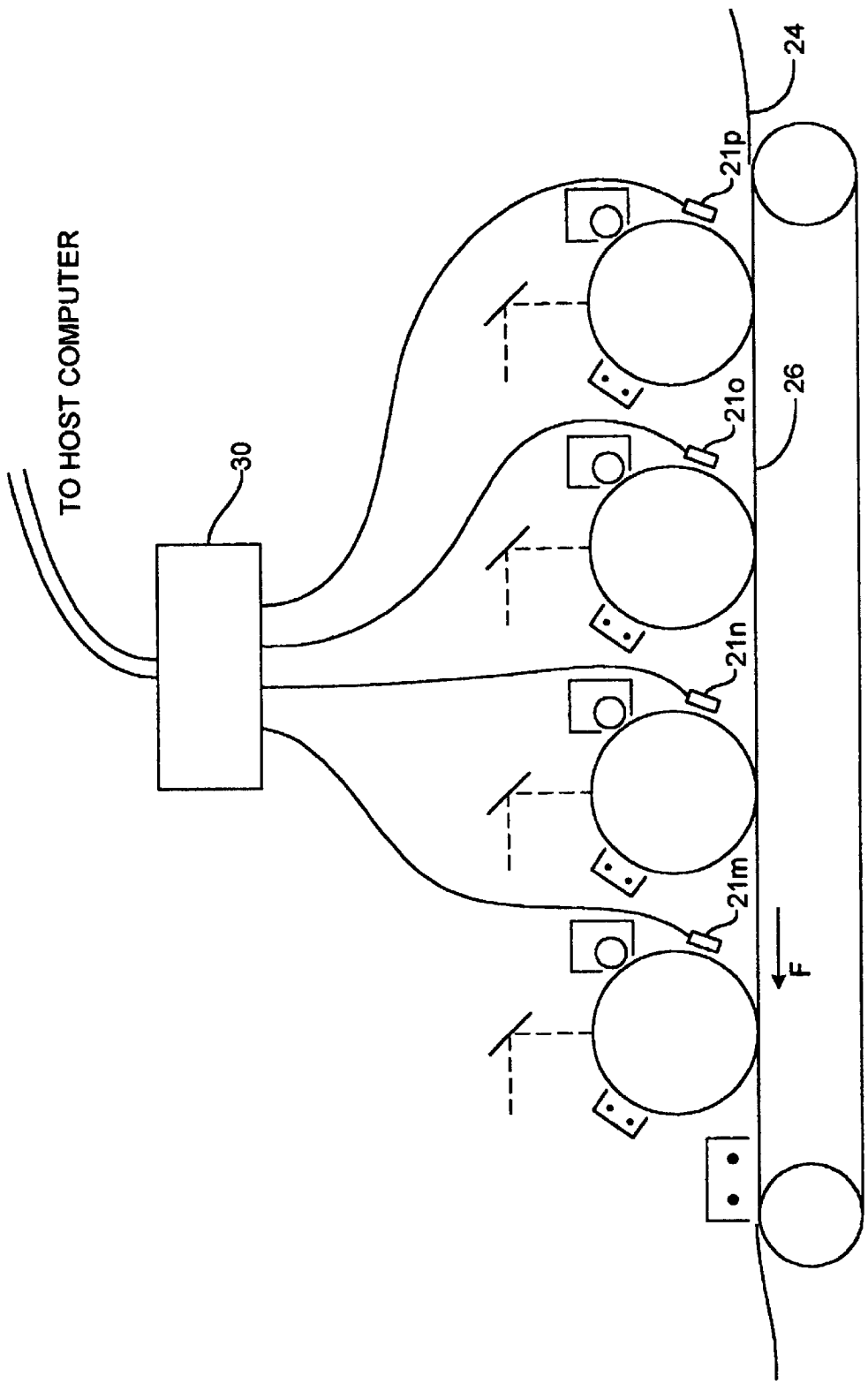
FIG. 5 is a multi-channel densitometer arrangement in an imaging machine with probes positioned for measurement in several color processing modules.

Turning now to FIG. 5, a four-color electrophotographic printer is shown, with a densitometer probe positioned in each color processing module. Probes 21m–21p monitor post-development density for the cyan, magenta, yellow, and black processing modules, respectively. The toner developed on each processing module drum is subsequently transferred to receiver sheets such as sheet 24, conveyed by transport belt 26 in the direction indicated by arrow "F".

All four probes are connected to controller circuit 30. The microcontroller of controller circuit 30 is programmed to output appropriate control signals to the probes, and receive the frequency output signals from the probes characterizing the density of toned test patches. Density data are computed, and previously saved base readings are subtracted to obtain net toner density values for each color processing module. Further data processing may include averaging individual readings, recording out-of-limit readings, calculating color balance, and calculating other known performance metrics and statistics. Only the summary results needed for designated purposes such as process control or quality data logging are output to the host computer or display.

Figure 6:
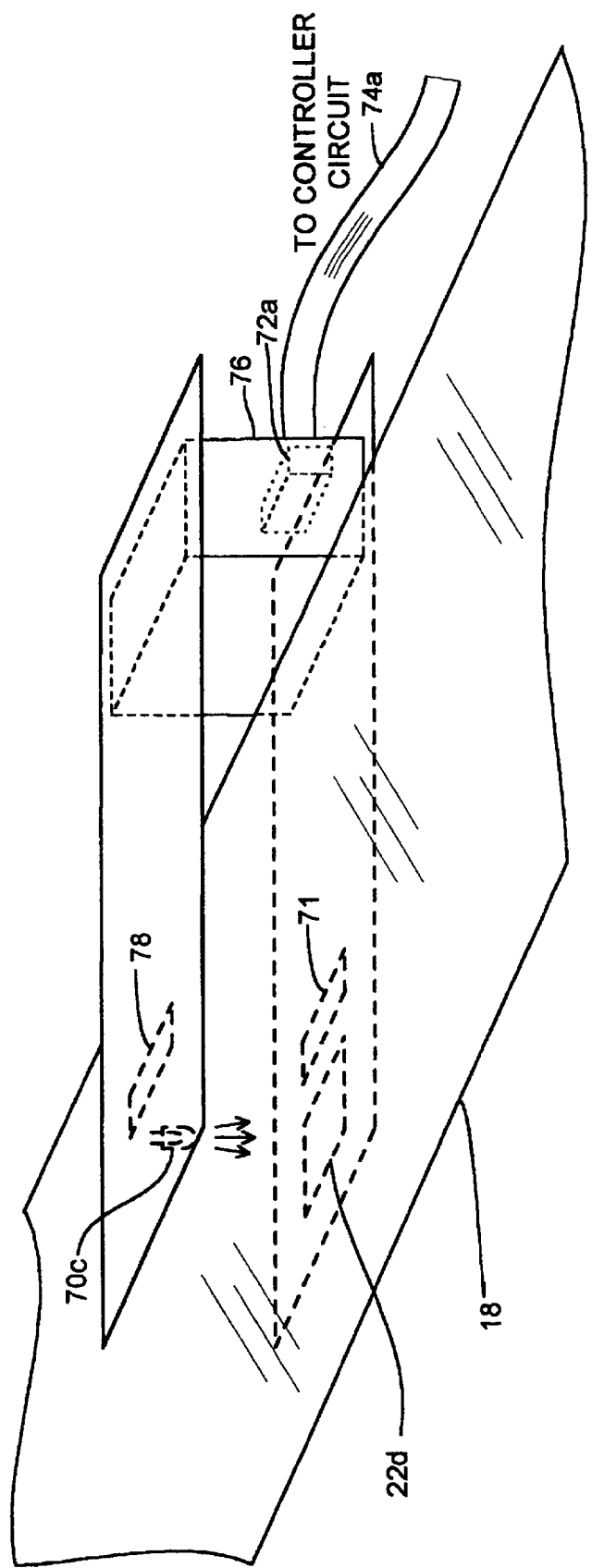
FIG. 6 is a detailed view of a probe for transmission densitometry.

FIG. 6 shows detail of a preferred probe for transmission densitometry. Light from LED 70c shines through transmissive web 18. The beam pattern emitted from LED 70c is typically broad and divergent, as indicated by the arrows. A portion of the emitted light is transmitted through web 18 and impinges on the L-to-F converter of sensor 22d. In general, discrete components may be used for L-to-F converter circuits. For small size and best noise immunity, the L-to-F converter is preferably an integrated circuit, such as Texas Advanced Optoelectronic Solutions, Inc. model TSL230 or TSL235.

The 8-pin TSL230 has pins for real time digital control of sensitivity and frequency divide-by ratio by the controller circuit This programmability facilitates measurement of a wide density range with good density resolution, and a fast density update rate. The non-programmable 3-pin TSL235 is a smaller and lower-cost circuit well suited to applications with less demanding requirements for density range, density resolution, or measurement update rate. The TSL235 can be a good choice for reflection densitometry, where density usually saturates well below 2.0 density units. Transmission densitometry often requires a larger range, depending on the application. Decoupling capacitor 71, standard for integrated circuits, stabilizes the L-to-F converter at its supply voltage pins.

Connector 72a and cable 74a provide connections between the probe and the controller circuit for power, control signals, and frequency output. If the cable length is greater than about 30 cm, a line driver or buffer (not shown) is recommended on the probe. Resistor 78 in series with LED 70c limits the current through LED 70c to the value needed, which depends on the LED type, the density range to be measured, the distance to the sensor, and the sensor type. Alternatively, the series resistor or other current control circuitry could be located external to the probe.

Depending on the spectral distribution of the light emitted from LED 70c, some sample materials, such as photoconductors, may be prone to damage, e.g., fogging, fatigue, or fading, after long exposure to LED 70c. In such cases, the current in LED 70c is limited to a small value, to minimize exposure intensity. Ideally LED 70c is deenergized when measurements are not needed, to minimize the cumulative exposure time. Pulse-mode operation is also effective in reducing exposure. These exposure-reducing measures may also reduce power requirements, heating, and slow the brightness degradation of LED 70c, and prolong its useful life. In these cases, circuitry for pulse modulation and deenergizing LED 70c is preferably located on the controller board (not shown in FIG. 6).

The sensitive area of the TSL230 and TSL235 is only about 1 mm$^2$. With such small light detectors, an LED with a wide uniform beam pattern is preferred, making accurate LED-to-sensor alignment less critical, and reducing alignment sensitivity. Perfect alignment is not essential, because the base reading saved previously is subtracted. The base reading is determined during calibration and depends on a number of factors, including spacing and alignment. To avoid density measurement error, spacing and alignment (or moderate misalignment) should remain fixed after calibration. A recalibration would typically be done at regular intervals or whenever spacing or alignment may have been disturbed.

The transmission type probe is preferably in the form of two circuit boards on opposite sides of web 18, as shown in FIG. 6, with sensor 22d on one board, and LED 70c on the other. Conducting traces on the boards and conductors between the two boards (not shown) connect the electronic components to connector 72a. The two boards are attached to mounting block 76, or equivalent joining parts forming a rigid U-shaped structure. This probe structure holds the LED-to-sensor alignment and spacing constant. The probe length extends from the connector end, just outside the edge of web 30, to a distance inside the edge positioning sensor 22d opposite the track of web 18 where measurements are needed. The probe width is minimized, leaving maximum space for work stations and other items that must be positioned near the web.

In an alternative transmission type probe structure, LED 70c may be mounted separately and independently from the probe. In a bench-top application, the light emitter may be in the form of a "light box" rather than an LED. Such a light box, available from Argraph Corp., also functions as the work surface supporting the sample and densitometer probe. In these cases the probe consists of only the one circuit board with sensor 22d and decoupling capacitor 71. The probe may then need to be carefully positioned with respect to LED 70c, so that LED 70c is aligned with sensor 22d on the probe.

Several approaches for mounting the probe on-board a machine are available. Slide rails (not shown) can be provided to engage the long edges of the probe circuit board or boards. This approach enables easy removal and insertion, such as for cleaning. It also defines the probe position in the process direction, and circuit board spacing from web 30. A stop in the slide rails, or a detent mechanism, may be provided for accurate cross-track positioning. Alternatively, for cantilever mounting, mounting block 76 at the connector end can be rigidly attached to a supporting structure.

Figure 7:
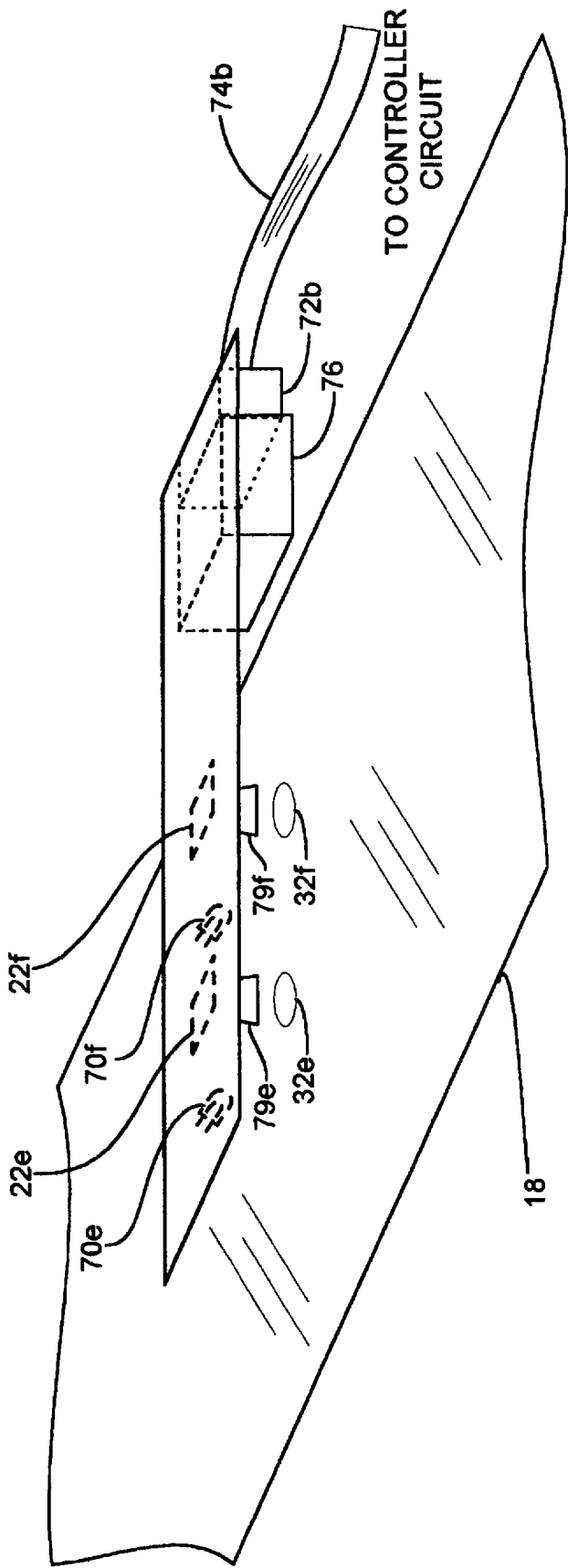
FIG. 7 is a detailed view of a probe for reflection densitometry.

FIG. 7 shows detail of a preferred probe for reflection densitometry. To illustrate that a probe may have multiple densitometer channels, this probe has two similar channels, for measurement in two cross-track positions. Each channel has its own LED and sensor. For one channel, light from LED 70e obliquely illuminates spot 32e of web 18. A portion of the light is diffusely reflected from spot 32e, and impinges on the L-to-F converter of sensor 22e. Light shield 79e blocks the direct path for light from LED 70e to sensor 22e, and other extraneous light. Thus sensor 22e receives only light reflected from spot 32e, illuminated by LED 70e. For smallest size and best noise immunity, sensor 22e preferably uses an integrated circuit L-to-F converter, as in the transmission type probe of FIG. 6. Decoupling capacitors (not shown in FIG. 7) are provided for each integrated circuit, as in FIG. 6. The mounting options for the reflection probe are also similar to those discussed for the transmission type probe of FIG. 6. A second reflection density channel in FIG. 7 uses LED 70f, which illuminates spot 32f. Reflected light from spot 32f impinges on the L-to-F converter of sensor 22f, shielded by light shield 79f.

With continuing reference to FIG. 7, cable 74b connects the probe to the controller circuit. Power, control signals, and frequency outputs are connected through connector 72b. Separate conductors are provided for the frequency outputs of the two channels. Series resistors (not shown in FIG. 7) are provided for LEDs 70e and 70f, as in the transmission type probe of FIG. 6. LED current is preferably limited to a small value sufficient for the application, especially if the sample is prone to damage by exposure to LED light emission, just as in the transmission type probe.

A variation from the probe configuration of FIG. 7 uses two LEDs of different peak emission wavelength, for a single channel. These two LEDs are aimed to obliquely illuminate the same sample spot directly opposite either sensor 22e or sensor 22f. The controller circuit energizes only one LED of any channel at any one time. To evaluate sample uniformity in the two tracks, LEDs of the same color are energized for both channels. Preferably, the LED color is such that good measurement sensitivity is obtained for the particular sample material and color. To measure test patches of different colors, the LED giving best measurement sensitivity is energized as the respective patches pass opposite either sensor 22e or sensor 22f.

Another variation from the probe configuration of FIG. 7 uses three LEDs of red, green, and blue peak emission wavelength, respectively, for a single channel. All three LEDs are aimed to obliquely illuminate the same sample spot. The controller circuit energizes the three LEDs one at a time in rapid sequence, to obtain red, green, and blue density measurements for a single sample area. For a web or test patch with mixed or layered colorants on a reflective support such as paper, the red, green, and blue density values together characterize the overall color of the sample. Such a configuration thus functions as a basic colorimeter. For better color discrimination, more than three LEDs, of differing peak emission wavelengths, can be used.

Figure 8:
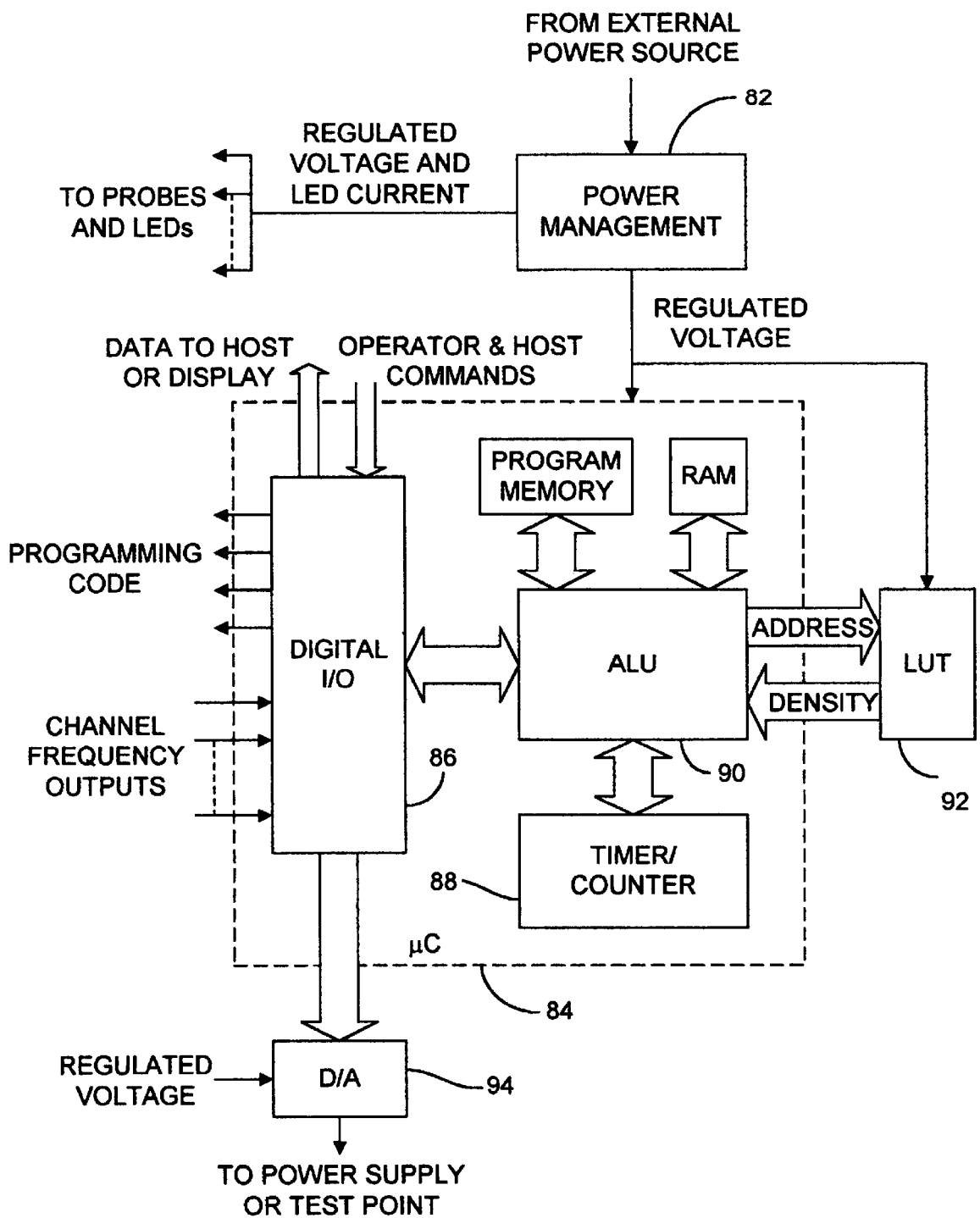
FIG. 8 is a functional block diagram of a controller circuit for multiple channels.

FIG. 8 shows a functional block diagram of a controller circuit connected to multiple densitometer channels. Microcontroller 84, such as Microchip Corp. model PIC16C622, includes timer 88 to measure the period of the frequency output signal from each channel. The frequency outputs input to digital I/O 86 of microcontroller 84. The period is measured in units of timer clock counts, yielding a period count. For a given frequency output signal from a probe, a higher timer clock frequency results in a larger period count, which in turn enables higher resolution in density LUT 92. The clock frequency of timer 88 is directly related to the master oscillator frequency of microcontroller 84.

If the probe light-to-frequency converter is programmable, microcontroller 84 outputs a programming code through digital I/O 86 for the sensitivity and/or frequency divide-by ratio such that a period count is obtained that is within a predetermined range. Since the channels are read one at a time, the same programming code output may be wired in common to all channels. For each channel, the period should be long enough to give adequate resolution in the period count, but short relative to the density measurement spot size divided by the process velocity. With a period this short, sample travel during the measurement is only a fraction of the spot diameter. This avoids excessive blur in reading a moving sample, and permits a fast measurement update rate.

For the TSL230 light-to-frequency converter, the sensitivity and divide-by ratio each have 2-bit codes, and each has two dedicated pins on the integrated circuit. Microcontroller 84 measures the period of the frequency outputs from the sensors of all channels one at a time in a rapid cycle. Microcontroller 84 outputs the same programming code in common to all the sensors. FIG. 8 shows a 4-wire programming output to the sensors, to program both the sensitivity and the divide-by ratio of the TSL230. If the density range to be covered is not too large, it may be adequate to program only one of the sensitivity or divide-by ratio, thus reducing by two the number of conductors in the cables to the probes. It may also be adequate to program only one of the two bits for the sensitivity or divide-by ratio. In such cases, the non-programmed bits are hard-wired on the probe.

Microcontroller 84 uses the period count, along with the sensitivity and/or divide-by ratio code if a programmable light-to-frequency converter is used, to form the address for entering LUT 92. LUT 92 may be within microcontroller 84 or may be contained in a separate nonvolatile memory as shown, such as a programmable read-only memory (PROM) integrated circuit. LUT 92 is preloaded with the scaled optical density values corresponding to the period count and the programming code. LUT 92 is addressed from arithmetic and logic unit (ALU) 90, and LUT 92 returns a scaled density value to ALU 90.

After obtaining a gross density value from LUT 92, a previously saved base density value is subtracted. Base density values are obtained in response to a "calibrate" command. The operator or the host computer commands a calibration reading when a reference sample, or a bare (untoned) web area, is in position for density measurement. Calibration may be repeated as often as necessary, to update and save the base reading. Further data processing may include calculating averages, uniformity, color balance, and transfer efficiency. Other statistical calculations and pattern recognition may be included according to the application. In some applications, only the summary results or exception reports needed for designated purposes such as process control or quality data logging need be output to the host computer or display. In other applications, all of the raw density readings may be made available to the host computer if needed.

Microcontroller 84 is programmed to service each channel in turn, so that processing time must be shared among the channels. The updated density values are obtained at a rate compatible with the process velocity, and the size of the test patches or other features that are to be measured. For example, consider a printer with a process velocity of 400 mm/s, requiring five readings within a test patch 20 mm square, for each of four channels. Let the effective measurement spot diameter on the test patch be 2 mm. Five readings within the 20 mm test patch correspond to a pitch of 20/5=4 mm. This pitch is larger than the 2 mm spot size, so the measurements are independent in the sense that the measurement spots do not overlap. The corresponding time between the patch readings for the one channel is 4/400= 0.01 seconds, or 10 milliseconds.

Continuing with the printer example, four channels must all be updated, so the time available for the microcontroller to process and update each channel is 10/4=2.5 milliseconds per channel. With this update time constraint, the period of the light-to-frequency converter can be no more than 2.5 milliseconds. During this time the web advances no more than 400×0.0025=1.0 mm, which is only half the 2 mm spot size, an acceptable amount of blur. Subject to the 2.5-millisecond update time constraint, the required density range (say, 3.0 density units) must be covered, at the required resolution (say, 0.01 density units). This is within the capability of the model TSL230 light-to-frequency converter, connected to a controller circuit with a typical microcontroller running with a master clock frequency of 20 MHz or faster.

With continuing reference to FIG. 8, power management 82 enables the multi-channel densitometer to be used in machine environments where power at the required voltage may not be available or may not be well regulated. Power management 82 provides well-regulated DC supply voltage not only to the controller circuit, but also through the connectors and cables to the sensors on the probes, and to the LED drive circuitry. This helps keep the probe size and component count small, and minimizes overall voltage regulator cost for the multi-channel densitometer. In some applications, LEDs are driven in a pulsed mode, and may be deenergized when measurements are not needed. In these cases, LED pulse modulation and deenergizing is included in power management 82.

The microcontroller may optionally output density readings to one or more digital-to-analog (D/A) converters, such as D/A converter 94. The output of D/A converter 94 may represent a single density channel in real time, or may be the result of a calculation such as a test patch average, or a difference between two channels, for example. As a troubleshooting aid, the analog output may be connected to a test point, which can be monitored with an ordinary voltmeter. An operator command to the controller circuit may select the channel or function to be output from D/A converter 94.

For process control purposes, the analog output may be input to an analog programmable power supply for a process work station. Through such a connection, a feedback loop is completed wherein the work station responds to the density measurements, driving the density toward the desired value. Alternatively, process control loops may be completed digitally, and may go through the connection to the host computer, with no need for a D/A converter.

CONCLUSION, RAMIFICATIONS, AND SCOPE

The preferred multi-channel densitometer has a single controller circuit for multiple measurement channels. Sensors for the multiple channels may be on separate, independently locatable probes, or on a single circuit board. Compared to the multiple single-channel densitometers required in the prior art for comparable functionality, the multi-channel densitometer has smaller probe size, fewer components, lower cost, and superior noise immunity. The controller circuit may be located away from the process medium to be measured, where space is not at a premium. The controller circuit collects readings from multiple channels, and digitally processes them to obtain both single-channel and multi-channel functions of density, such as uniformity, transfer efficiency, and color balance. These advantages make it economically feasible to use the multi-channel densitometer for process monitoring and control in small, moderate-cost machines. The invention also makes multi-channel bench-top densitometers affordable where budgets are most limited, as in amateur photo labs, and student laboratories, for example.

The invention has been described in detail with particular reference to preferred embodiments thereof, but it will be understood that variations and modifications can be effected within the spirit and scope of the invention.

What is claimed is:

1. A multi-channel densitometer for measuring optical density of sample areas, said densitometer comprising:
   from 3 to 8 sensors distributed on a probe and facing said sample areas, such that each said sensor receives light impinging first upon the sample area opposite said sensor, and thence from said sample area to a light detector of said sensor, and has an output characteristic of the light intensity incident on said light detector, and
   a controller circuit electrically connected to each said sensor, said controller circuit providing power to said sensors, and receiving said outputs from said sensors;

whereby said controller circuit collects signals characteristic of the optical density of said sample areas at positions opposite the respective sensors.

2. A multi-channel densitometer as set forth in claim 1, and further including an output of optical density values to a receiving device from the group consisting of host computers, networks, alphanumeric displays, graphic displays, digital storage devices, digital-to-analog converters, and means for adjusting subsequent sample processing.

3. A multi-channel densitometer as set forth in claim 1, and further including means to compute a multi-channel function of optical density from the group of function types consisting of uniformity, net density, transfer efficiency, and color.

4. A multi-channel densitometer as set forth in claim 3, and further including an output of a multi-channel function of optical density to a receiving device from the group consisting of host computers, networks, alphanumeric displays, graphic displays, digital storage devices, digital-to-analog converters, and means for adjusting subsequent sample processing.

5. A multi-channel densitometer as set forth in claim 1, and further including, for each said sensor, a light emitter, where said light emitter emits light impinging first upon the sample area opposite said sensor, and thence from said sample area to said light detector, said emitter and said light detector forming an emitter pair.

6. A multi-channel densitometer as set forth in claim 5, wherein at least one said emitter detector pair comprises a spectrally broad-band or white light emitter and a detector with a limited band of spectral responsivity, whereby the optical density of said sample areas can be measured in the color corresponding to the spectral responsivity.

7. A multi-channel densitometer as set forth in claim 5, wherein said light emitters are light emitting diodes.

8. A multi-channel densitometer as set forth in claim 5, wherein a plurality of said emitter pairs are of differing emitter color or peak wavelength, whereby when said sample areas are of differing colors, they can be measured with high sensitivity using light of complementary colors to the respective areas, and whereby said sample areas of the same color can be characterized in color by a set of measurements using light of different colors.

9. A multi-channel densitometer as set forth in claim 1, and further including, for at least one said sensor, a plurality of light emitters of differing color or peak emission wavelength, selectively energized one at a time, illuminating substantially the same sample spot opposite said sensor, whereby said sample areas of differing colors, in the same cross-track position, can be measured in turn with high sensitivity as said sample areas pass, by using light of complementary color to the respective areas.

10. A multi-channel densitometer as set forth in claim 1, and further including, for at least one said sensor, a set of three light emitters of red, green, and blue color, successively energized one at a time, illuminating substantially the same sample spot opposite said sensor, whereby a set of three output values of said sensor characterizes the color of said sample area.

11. A multi-channel densitometer for measuring optical density of sample areas, said densitometer comprising:

from 2 to 8 independently locatable probes, having in total from 3 to 8 sensors facing said sample areas, such that each said sensor receives light impinging first upon the sample area opposite said sensor, and thence from said sample area to a light detector of said sensor, and has an output characteristic of the light intensity incident on said light detector; and a controller circuit electrically connected to each said probe, said controller circuit providing power to said sensors, and receiving said outputs from said sensors;

whereby said controller circuit collects signals characteristic of the optical density of said sample areas at positions opposite the respective sensors.

12. A multi-channel densitometer as set forth in claim 11, and further including an output of optical density values to a receiving device from the group consisting of host computers, networks, alphanumeric displays, graphic displays, digital storage devices, digital-to-analog converters, and means for adjusting subsequent sample processing.

13. A multi-channel densitometer as set forth in claim 11, and further including means to compute a multi-channel function of optical density from the group of function types consisting of uniformity, net density, transfer efficiency, and color.

14. A multi-channel densitometer as set forth in claim 13, and further including an output of a multi-channel function of optical density to a receiving device from the group consisting of host computers, networks, alphanumeric displays, graphic displays, digital storage devices, digital-to-analog converters, and means for adjusting subsequent sample processing.

15. A multi-channel densitometer as set forth in claim 11, and further including, for each said sensor, a light emitter, where said light emitter emits light impinging first upon the sample area opposite said sensor, and thence from said sample area to said sensor, said emitter and said light detector forming an emitters-detector pair.

16. A multi-channel densitometer as set forth in claim 15, wherein at least one said emitter-pair comprises a spectrally broad-band or white light emitter and a detector with a limited band of spectral responsivity, whereby the optical density of said sample areas can be measured in the color corresponding to the spectral responsivity.

17. A multi-channel densitometer as set forth in claim 15, wherein a plurality of said emitter-detector pairs are of differing emitter color or peak wavelength, whereby when said sample areas are of differing colors, they can be measured with high sensitivity using light of complementary colors to the respective areas, and whereby said sample areas of the same color can be characterized in color by a set of measurements using light of different colors.

18. A multi-channel densitometer as set forth in claim 11, and further including, for at least one said sensor, a plurality of light emitters of differing color or peak emission wavelength, selectively energized one at a time, illuminating substantially the same sample spot opposite said sensor, whereby said sample areas of differing colors, in the same cross-track position, can be measured in turn with high sensitivity as said sample areas pass, by using light of complementary color to the respective areas.

19. A multi-channel densitometer as set forth in claim 11, and further including, for at least one said sensor, a set of three light emitters of red, green, and blue color, successively energized one at a time, illuminating substantially the same sample spot opposite said sensor, whereby a set of three output values of said sensor characterizes the color of said sample area.

20. A multi-channel densitometer for measuring optical density of sample areas. said densitometer comprising:

from 2 to 8 independently locatable probes each having from 1 to 8 sensors facing said sample areas, such that each said sensor receives light impinging first upon the sample area opposite said sensor, and thence from said sample area to a light detector of said sensor, and has an output characteristic of the light intensity incident on said light detector; and a controller circuit electrically connected to each said probe, said controller circuit providing power to said sensors and receiving said outputs from said sensors;

wherein a plurality of said probes are of different length from each other, each having a sensor at one end, and mounted with the other end opposite the sample edge;

whereby density measurements are obtained at distances from the sample edge according to the lengths of said probes.

* * * * *

UNITED STATES PATENT AND TRADEMARK OFFICE
CERTIFICATE OF CORRECTION

PATENT NO. : 6,671,052 B1
DATED : December 30, 2003
INVENTOR(S) : Allen J. Rushing It is certified that error appears in the above-identified patent and that said Letters Patent is hereby corrected as shown below:

Column 3,
Line 67, delete "dk".

Column 5,
Line 22, delete the hyphenation of "to-the".
Line 33, change "mating" to -- making --.

Column 8,
Line 64, delete "A-s".

Column 9,
Line 5, delete the number "25".
Line 30, delete "LR".

Column 11,
Lines 17 and 39, change "30" to -- 18 --.

Column 15,
Lines 23-34, Claims 5 and 6 should read:

5.   A multi-channel densitometer as set forth in claim1, and further including, for each said sensor, a light emitter, where said light emitter emits light impinging first upon the sample area opposite said sensor, and thence from said sample area to said light detector, said emitter and said light detector forming an emitter-detector pair.

6.   A multi-channel densitometer as set forth in claim 5, wherein at least one said emitter-detector pair comprises a spectrally broad-band or white light emitter and a detector with a limited band of spectral responsivity, whereby the optical density of said sample areas can be measured in the color corresponding to the spectral responsivity.

Lines 37-44, Claim 8 should read:

8.   A multi-channel densitometer as set forth in claim 5, wherein a plurality of said emitter-detector pairs are of differing emitter color or peak wavelength, whereby when said sample areas are of differing colors, they can be measured with high sensitivity using light of complementary colors to the respective areas, and whereby said sample areas of the same color can be characterized in color by a set of measurement using light of different colors.

UNITED STATES PATENT AND TRADEMARK OFFICE
CERTIFICATE OF CORRECTION

PATENT NO. : 6,671,052 B1
DATED : December 30, 2003
INVENTOR(S) : Allen J. Rushing It is certified that error appears in the above-identified patent and that said Letters Patent is hereby corrected as shown below:

Column 16,
Lines 28-39, Claims 15 and 16 should read:

15. A multi-channel densitometer as set forth in claim 11, and further including, for each said sensor, a light emitter, where said light emitter emits light impinging first upon the sample area opposite said sensor, and thence from said sample area to said sensor, said emitter and said light detector forming an emitters-detector pair.

16. A multi-channel densitometer as set forth in claim 15, wherein at least one said emitter-detector pair comprises a spectrally broad-band or white light emitter and a detector with a limited band of spectral responsivity, whereby the optical density of said sample areas can be measured in the color corresponding to the spectral responsivity.

Signed and Sealed this

Twenty-third Day of March, 2004

JON W. DUDAS
*Acting Director of the United States Patent and Trademark Office*

(12) EX PARTE REEXAMINATION CERTIFICATE (6403rd)

United States Patent
Rushing

(10) Number: US 6,671,052 C1
(45) Certificate Issued: Aug. 26, 2008

(54) MULTI-CHANNEL DENSITOMETER

(76) Inventor: Allen Joseph Rushing, 429 Tara La., Webster, NY (US) 14580

Reexamination Request:
No. 90/007,765, Oct. 5, 2005

Reexamination Certificate for:
Patent No.: 6,671,052
Issued: Dec. 30, 2003
Appl. No.: 09/873,465
Filed: Jun. 4, 2001

Certificate of Correction issued Mar. 23, 2004.

(51) Int. Cl.
*G01N 21/59* (2006.01)

(52) U.S. Cl. .................... 356/446; 356/429; 356/430
(58) Field of Classification Search ............... None See application file for complete search history.

(56) References Cited

U.S. PATENT DOCUMENTS

| 3,756,725 A | | 9/1973 | Manring |
| 3,762,817 A | * | 10/1973 | Harklau ............... 356/73 |
| 3,930,447 A | * | 1/1976 | Murray ............... 101/365 |
| 4,512,662 A | | 4/1985 | Tobias |
| 4,806,002 A | | 2/1989 | Simeth et al. |
| 2002/0097454 A1 | | 7/2002 | Gudaitis |

* cited by examiner

*Primary Examiner*—Erik Kielin

(57) ABSTRACT

A multi-channel densitometer has a light sensor for each channel. The channels may be on a single circuit board, or may be on small, independently locatable probes. The outputs from the sensors are input to a single conveniently located controller circuit. The controller circuit provides power and control signals to the sensors, and processes the sensor outputs to obtain sample optical density. The multi-channel configuration saves space where the density measurements are needed, reduces the component count and cost, and facilitates calculation of multi-channel density functions, such as uniformity, transfer efficiency and color balance.

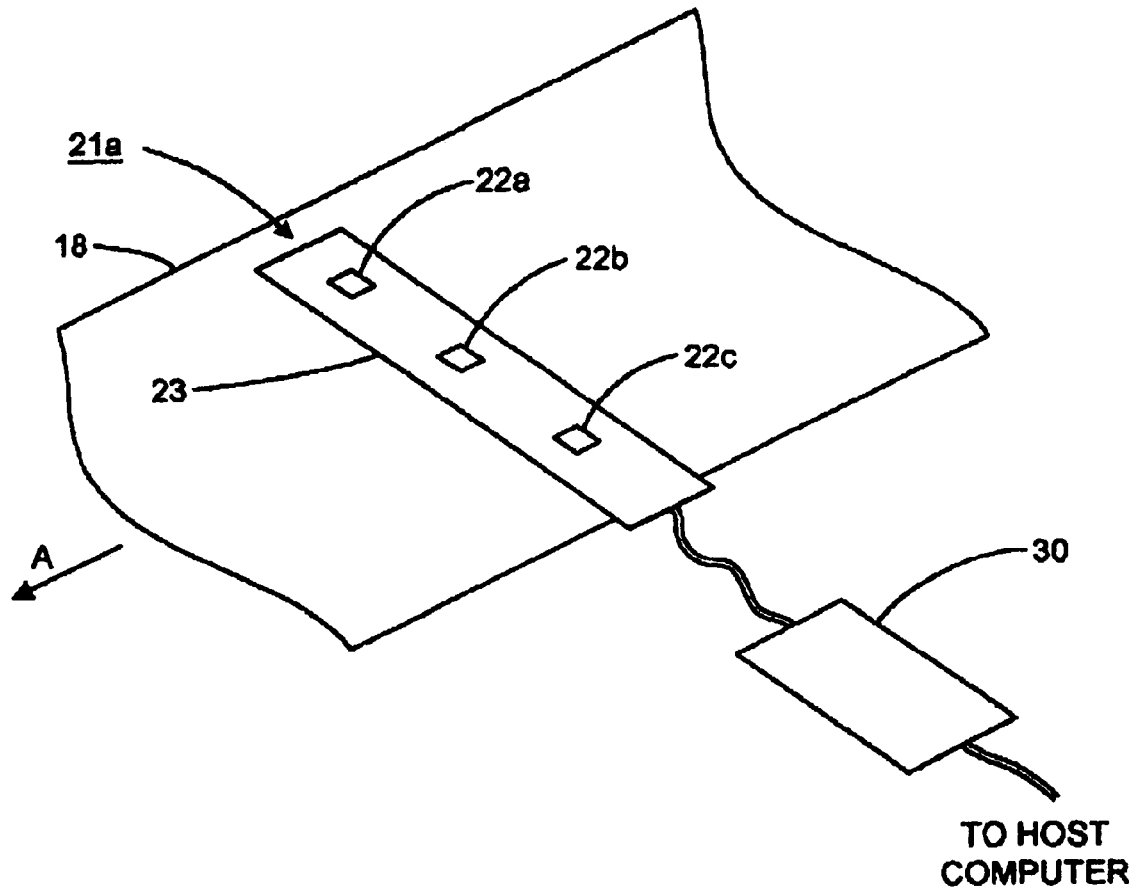

US 6,671,052 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 4, 8–10 and 20 is confirmed.

Claims 1, 2 and 5–7 are cancelled.

Claims 11, 15 and 16 are determined to be patentable as amended.

Claims 12–14 and 17–19, dependent on an amended claim, are determined to be patentable.

New claims 21–25 are added and determined to be patentable.

11. A multi-channel densitometer for measuring optical density of sample areas, said densitometer comprising:
from 2 to 8 independently locatable probes, having in total from 3 to 8 sensors *permanently affixed to said probes, and* facing said sample areas, such that each said sensor receives light impinging first upon the sample area opposite said sensor, and thence from said sample area to a light detector of said sensor, and has an output characteristic of the light intensity incident on said light detector, *and such that after said probes are mounted in fixed position for said measuring, said probes remain immobilized by mechanical disengagement and isolation from adjustment, rendering positional adjustment unavailable during measurement use, until said probes are relocated*; and
a controller circuit electrically connected to each said probe, said controller circuit providing power to said sensors, [and] receiving said outputs from said sensors, *and outputting signals characteristic of the optical density of every individual one of said sample areas*;
whereby said controller circuit collects signals characteristic of the optical density of *each one of* said sample areas, *and said densitometer measures the optical density of each one of said sample areas*, at positions opposite the respective sensors.

15. A multi-channel densitometer as set forth in claim 11, and further including, *separately* for each said sensor, a *single* light emitter, where said light emitter emits light impinging first upon the sample area opposite said sensor, and thence from said sample area to said [sensor, said emitter and said light detector forming an emitters-detector pair] *light detector, said light emitters and said light detectors being equal in number and operating as emitter-detector pairs to obtain signals characteristic of the optical density of each said sample area.*

16. A multi-channel densitometer as set forth in claim 15, wherein at least one said emitter-detector pair comprises a spectrally broad-band or white light emitter and a [detector] *sensor with a limited band of spectral responsivity, whereby the optical density of said sample areas can be measured in the color corresponding to the spectral responsivity.*

21. *A multi-channel densitometer for measuring optical density of sample areas, said densitometer comprising:*
*from 3 to 8 sensors distributed on a probe and facing said sample areas, such that each said sensor receives light impinging first upon the sample area opposite said sensor, and thence from said sample area to a light detector of said sensor, and has an output characteristic of the light intensity incident on said light detector; and*
*a controller circuit electrically connected to each said sensor, said controller circuit providing power to said sensors, and receiving said outputs from said sensors;*
*and further including, for each said sensor, a light emitter, where said light emitter emits light impinging first upon the sample area opposite said sensor, and thence from said sample area to said light detector, said emitter and said light detector forming an emitter-detector pair;*
*wherein a plurality of said emitter-detector pairs are of differing emitter color or peak wavelength;*
*whereby said controller circuit collects signals characteristic of the optical density of said sample areas at positions opposite the respective sensors; and*
*whereby when said sample areas are of differing colors, said sample areas can be measured with high sensitivity using light of complementary colors to the respective areas, and whereby said sample areas of the same color can be characterized in color by a set of measurements using light of different colors.*

22. *A multi-channel densitometer capable of simultaneously measuring optical density of a plurality of separate non-overlapping sample areas, said densitometer comprising:*
*from 3 to 8 sensors distributed on a probe supporting all said sensors in permanent fixed position relative to each other, with said sensors facing said sample areas, such that each said sensor receives light impinging first upon the sample area opposite said sensor, and thence from said sample area to a light detector of said sensor, and has an output characteristic of the light intensity incident on said light detector, and such that after said probe is mounted in fixed position for said measuring, said probe remains immobilized by mechanical disengagement and isolation from adjustment, rendering positional adjustment unavailable during measurement use, until said probe is relocated; and*
*a controller circuit electrically connected to each said sensor, said controller circuit providing power to said sensors, receiving said outputs from said sensors, and outputting signals characteristic of the optical density of every individual one of said sample areas;*
*whereby said controller circuit collects signals characteristic of the optical density of each one of said sample areas, and said densitometer measures the optical density of each one of said sample areas, at positions opposite the respective sensors.*

23. *A multi-channel densitometer as set forth in claim 22, and further including, separately for each said sensor, a single light emitter, where said light emitter emits light impinging first upon the sample area opposite said sensor, and thence from said sample area to said light detector, said light emitters and said light detectors being equal in number and operating as emitter-detector pairs to obtain signals characteristics of the optical density of each said sample area.*

24. A multi-channel densitometer as set forth in claim 23, wherein at least one said emitter detector pair comprises a spectrally broad-band or white light emitter and a detector with a limited band of spectral responsivity, whereby the optical density of said sample areas can be measured in the color corresponding to the spectral responsivity.

25. A multi-channel densitometer as set forth in claim 22, and further including an output of optical density values to a receiving device from the group consisting of host computers, networks, alphanumeric displays, graphic displays, digital storage devices, digital-to-analog converters, and means for adjusting subsequent sample processing.

* * * * *